United States Patent [19]
Oda et al.

[11] Patent Number: 5,725,874
[45] Date of Patent: Mar. 10, 1998

[54] SOLUBILIZER AND EXTERNAL PREPARATIONS CONTAINING THE SAME

[75] Inventors: Hideshi Oda; Tetsuro Tateishi; Akira Nakagawa; Munehiko Hirano; Koki Shoho, all of Tosu, Japan

[73] Assignee: Hisamitsu Pharmaceutical Co., Inc., Tosu, Japan

[21] Appl. No.: 553,615

[22] PCT Filed: May 18, 1994

[86] PCT No.: PCT/JP94/00800

§ 371 Date: Nov. 16, 1995

§ 102(e) Date: Nov. 16, 1995

[87] PCT Pub. No.: WO94/26309

PCT Pub. Date: Nov. 24, 1994

[30] Foreign Application Priority Data

May 19, 1993 [JP] Japan ................. 5-139224

[51] Int. Cl.$^6$ ............................ A61F 13/00
[52] U.S. Cl. ............ 424/443; 424/447; 424/448; 424/449; 424/401; 424/45; 514/937; 514/944; 514/945; 514/969
[58] Field of Search ............ 424/45, 443, 447, 424/448, 401, 484; 514/944, 945, 937, 969

[56] References Cited

U.S. PATENT DOCUMENTS 4,459,425   7/1984   Amano et al. ................. 568/666

FOREIGN PATENT DOCUMENTS 0080148    6/1983   European Pat. Off. .
63-264522  11/1988  Japan .

OTHER PUBLICATIONS

Chemical Abstracts, vol. 110, No. 18, May 1, 1989, Columbus, Ohio, US; Abstract No. 160412, XP002014010.

*Primary Examiner*—Raj Bawa
*Attorney, Agent, or Firm*—Bucknam and Archer

[57] ABSTRACT

Percutaneously absorbable preparations which comprise, by weight, 0.001 to 20%, preferably 0.1 to 20%, of 3-1-menthoxy-propane-1,2-diol as a solubilizer for a drug and 0.001 to 20%, preferably 0.5 to 10%, of the drug as two essential ingredients, the balance being other ingredients as adjuvants selected from water-soluble polymers, monohydric alcohols, polyhydric alcohols, rosin esters, water, fatty acid esters, hydrocarbons, softening agents, emulsifying agents. The preparations are in the forms of poultice, plasters, ointments, gels, creams, gel-like creams, lotions, reserver patches, liniments, aerosols and may be used in packs.

27 Claims, 1 Drawing Sheet

SOLUBILIZER AND EXTERNAL PREPARATIONS CONTAINING THE SAME

TECHNICAL FIELD

The present invention relates to a solubilizing agent or solubilizer for a pharmaceutically effective ingredient and an external preparation containing the solubilizer. In particular, the present invention relates to a solubilizer for an efficacious ingredient used in a percutaneously absorbable preparation such as poultice or for a fat-soluble powder used in a pack, the solubilizer being excellent in solubilization of such an effective ingredient as well as in safety, stability, compatibility, non-odorousness and refreshing, effect, and also relates to an external preparation containing the solubilizer.

BACKGROUND ART

Up to this time, many attempts have been made to attain desirable curative effects by the percutaneous absorption of drugs. It is a significant problem in such percutaneously absorbable preparations how efficiently the drug (active ingredient as a drug) is released from the base, i.e., how efficiently the drug migrates from the base to the skin. In general, when attempting to design a preparation using some drug therein, there frequently occurs a case that the drug crystallizes in the base because of its insufficient dissolution therein, resulting in poor drug release so that a sufficient curative effect is not achieved. Accordingly, the selection of an optimum solubilizer for a drug is an important factor in designing such a preparation. If an unsuitable solubilizer is selected for a drug, the release of the drug from the base is lowered due to the insufficient dissolution of the drug in the base, which leads to poor migration of the drug to an affected part so that poor curative effect results.

Solubilizers currently used for drugs include alcohols, glycols, several surfactants, essential oils such as peppermint oil, crotamiton, methyl salicylate, glycol salicylate and fatty acid esters such as isopropyl myristate.

For example, Japanese Pat. Appln. Laid-Open Gazette No. 154413/1981 discloses an anti-inflammatory agent for external use which comprises both an oil-in-water emulsion containing a solution of flurbiprofen in a terpene or in a fatty acid ester and an aqueous base, and Japanese Pat. Appln. Laid-Open Gazette No. 98209/1982 discloses another anti-inflammatory agent for external use which is prepared by dissolving indomethacin in a mono- or polyhydric alcohol or the like.

However, these solubilizers have problems because they have poor solubilizability (capability of solubilization) to cause the crystallization of a drug, they are limited in use due to their odors, they bleed from the base with the lapse of time due to their poor compatibility with the base, they are poor in stability to cause decomposition or discoloration with the lapse of time and they cause undesirable side effects due to their stimuli to the skin, resulting in unsatisfactory effects in many cases.

Meanwhile, attempts have been made to get a powder which is soluble in fat or difficultly soluble in water (hereinafter referred to as "fat-soluble powder") to be contained in a pack for its practical use. However, a pack generally comprises a water-soluble base which exhibits extremely poor solubilizability for a fat-soluble powder, so that many of the above attempts were accompanied by the problems that the solubilization of the powder in the base was difficult and/or that the resulting pack was poor in stability to cause crystallization of the powder with the lapse of time even when the powder could be solubilized in the base in the preparation stage.

SUMMARY OF THE INVENTION

The present invention aims at solving the above problems to provide a solubilizer which exhibits excellent solubilizability for a pharmaceutically effective ingredient and is excellent in safety, stability and compatibility, and provides an external preparation containing the solubilizer.

The above object of the present invention can be attained by using 3-l-menthoxypropane-1,2-diol as the solubilizer for a pharmaceutically effective ingredient.

Namely, the present invention resides in a solubilizer for a pharmaceutically effective ingredient which is composed of 3-l-menthoxypropane-1,2-diol, and in an external preparation containing the solubilizer and a pharmaceutically effective ingredient.

The term "pharmaceutically effective ingredient" used in this specification refers to a drug used in a percutaneously absorbable preparation or a fat-soluble powder used in a pack.

3-l-menthoxypropane-1,2-diol which is the solubilizer of the present invention, is a known substance described in, e.g., Japanese Pat. Appln. Laid-Open Gazette No. 88334/1983 as a substance having a cooling or refreshing activity. Further, Japanese Pat. Appln. Laid-Open Gazette No. 25908/1985 discloses that this compound is useful as a cosmetic material, has an excellent cooling effect and is extremely safe for the skin. However, there has not been made even any attempt to solubilize a pharmaceutically effective ingredient such as a drug by using said known substance, to say nothing of an attempt to get a drug solubilized by use of this substance to be absorbed percutaneously. In other words, such an attempt has been made for the first time by the inventors of the present invention and the present invention is based on this entirely new finding.

According to the present invention, the amount of 3-l-menthoxypropane-1,2-diol contained in an external preparation is 0.001 to 20% by weight of the total amount of the external preparation.

In particular, when the external preparation is a percutaneously absorbable preparation containing a drug as the effective ingredient and 3-l-menthoxypropane-1,2-diol is used as a solubilizer, the amount of 3-l-menthoxypropane-1,2-diol used will be 0.1 to 20% by weight, preferably 0.5 to 10% by weight, of the total amount of the external preparation. When the amount is less than 0.1% by weight, no sufficient effects as the solubilizer will be exhibited, while when it exceeds 20% by weight, no stable preparation will be prepared.

The drug to be used in the percutaneously absorbable preparation which is one of the external preparations according to the present invention is not particularly limited but may be any one selected from among known conventional drugs. Such drugs include steroidal anti-inflammatory agents such as prednisolone, dexamethasone, hydrocortisone, fluocinolone acetonide, betamethasone valerate, betamethasone dipropionate, clobetasone butyrate and prednisolone succinate; nonsteroidal anti-inflammatory agents such as indomethacin, diclofenac, ibuprofen, ketoprofen, flufenamic acid, ketorolac, flurbiprofen, felbinac, suprofen, pranoprofen, tiaprofen, loxoprofen and tenidap, and their ester derivatives; antiallergic agents such as tranilast, azelastine, ketotifen, ibudilast and emedastine; antihistamic agents such as diphenhydramine, chlorpheniramine, promethazine and tripelennamihe; central nervous system stimulants such as chlorpromazine, nitrazepam, diazepam, phenobarbital and reserpine; hormones such as insulin, testosterone, norethisterone, methyltestosterone, progesterone and estradiol; antihypertensive agents such as clonidine, reserpine and guanethidine sulfate; cardiotonics such as digitoxin and digoxin; antiarrhythmic agents such as propranolol hydrochloride, procainamide hydrochloride, ajimalin, pindolol and tulobuterol hydrochloride; coronary vasodilators such as nitroglycerin, isosorbide dinitrate, papaverine hydrochloride and nifedipine; local anesthetics such as lidocaine, benzocaine, procaine hydrochloride and tetracaine; analgetic agents such as morphine, aspirin, codeine, acetanilide and aminopyrine; skeletal muscle relaxants such as eperisone, tizanidine, tolperisone and inaperisone; antifungal agents such as acetophenylamine, nitrofurazone, pentamycin, naphthiomate, miconazole, omoconazole, clotrimazole, butenafine hydrochloride and bifonazole; antineoplastic agents such as 5-fluorouracil, busulfan, actinomycin, bleomycin and mitomycin; antidysurics such as terodiline hydrochloride and oxybutynin hydrochloride; antiepileptics such as nitrazepam and meprobamate; antiparkinson agents such as chlorzoxazone and levodopa; assistant to the prohibition of smoking such as nicotine; vitamins and prostaglandin, though the drug usable in the percutaneously absorbable preparation is of course not limited to them.

The amount of the drug used is preferably 0.001 to 20% by weight, more preferably 0.5 to 10% by weight, of the total amount of the external preparation, though it is not particularly limited.

The dosage form of the percutaneously absorbable preparation of the present invention is not particularly limited, but may be any one selected from among conventional poultice, plaster, ointment, gel, cream, gel-type cream, lotion, reserver-type patch, liniment, aerosol and so forth.

The poultice and plaster according to the present invention will now be described below.

In preparing the poultice, a hydrophilic base comprising a water-soluble polymer, a polyhydric alcohol and water is used in consideration of long-term stability, releasability, percutaneous absorbability and safety for the skin.

The water-soluble polymer to be used in the hydrophilic base may be one or more members suitably selected from the group consisting of gelatin, casein, pullulan, dextran, sodium alginate, soluble starch, carboxystarch, dextrin, carboxymethylcellulose, sodium carboxymethylcellulose, methylcellulose, ethylcellulose, hydroxyethylcellulose, polyvinyl alcohol, polyethylene oxide, polyacrylic acid, polyacrylamide, polysodium acrylate, polyvinylpyrrolidone, carboxyvinyl polymer, polyvinyl ether, methoxyethylenemaleic anhydride copolymer, isobutylenemaleic anhydride copolymer, N-vinylacetamide, copolymer comprising N-vinylacetamide and acrylic acid and/or acrylate salt and so forth. The amount of the water-soluble polymer used is 1 to 30% by weight, preferably 1 to 20% by weight, more preferably 1 to 15% by weight, based on the total amount of the preparation. When the amount is less than 1% by weight, the resulting preparation will have too low a viscosity to retain its shape, while when it exceeds 30% by weight, the resulting mixture of the constituents will have a high viscosity to lower the workability in preparing a homogeneous dispersion of the constituents or in applying the dispersion.

The polyhydric alcohol is one or more members suitably selected from the group consisting of polyethylene glycol, propylene glycol, dipropylene glycol, polypropylene glycol, 1,3-butylene glycol, 1,4-butylene glycol, isobutylene glycol, glycerol, diglycerol, sorbitol and so forth. The amount of the polyhydric alcohol used is 10 to 90% by weight, preferably 10 to 70% by weight, more preferably 20 to 60% by weight. When the amount is less than 10% by weight, the resulting preparation will exhibit poor humectant effect, while when it exceeds 90% by weight, the solubility of the water-soluble polymer will be adversely affected. The amount of water used is 10 to 90% by weight, preferably 20 to 80% by weight. The water serves to solubilize the water-soluble polymer to thereby make the polymer develop its thickening, cohesive and shape-retaining properties.

If necessary, the base of the poultice may further contain one or more crosslinking agents in addition to the above essential components. The crossliking agents include polyvalent metal compounds such as aluminum hydroxide, aluminum chloride, calcium hydroxide, calcium chloride, aluminum sulfate, aluminum ammonium sulfate, aluminum potassium sulfate, magnesium aluminometasilicate and dihydroxyaluminum aminoacetate; and compounds each having at least two epoxy groups in the molecule such as ethylene glycol diglycidyl ether, polyethylene glycol diglycidyl ether, propylene glycol diglycidyl ether, polypropylene glycol diglycidyl ether, polytetramethylene glycol diglycidyl ether, glycerol polyglycidyl ether, polyglycerol polyglycidyl ether, sorbitol polyglycidyl ether, sorbitan polyglycidyl ether, trimethylolpropane polyglycidyl ether, pentaerythritol polyglycidyl ether, resorcinol diglycidyl ether, neopentyl glycol diglycidyl ether and 1,6-hexanediol diglycidyl ether.

Further, the base of the poultice may contain one or more additives suitably selected from among fillers such as kaolin, zinc oxide, titanium dioxide, talc, bentonite and synthetic aluminum silicate; antiseptics such as thymol, methyl paraben and ethyl paraben; antioxidants such as ascorbic acid, stearic esters, dibutylhydroxytoluene, butylhydroxyanisole, gallic esters, vitamin E, vitamin E acetate and disodium edetate; ultraviolet absorbers such as 2-hydroxy-4-methoxybenzophenone, ethyl p-aminobenzoate, 2-(2-hydroxy-5-methylphenyl)benzotriazole, glycol salicylate, methyl salicylate and phenyl salicyalte; and emulsifying agents such as fatty acid esters of sorbitan, fatty acid esters of glycerol, fatty acid esters of decaglycerol, fatty acid esters of polyoxyethylene sorbitan, fatty acid esters of polyethylene glycol and polyoxyethylene alkyl ethers.

It is essential that the support of the poultice is made of a material which has no influence on the release of a drug, i.e., that the support neither interacts with a drug nor adsorb a drug. The support is selected from the group consisting of films and sheets of polyethylene, polypropylene, polyvinyl chloride, polyester, nylon and polyurethane; porous materials, expanded materials and woven and nonwoven fabrics of these polymers; laminates each comprising one or more members selected from the group consisting of these films and sheets and one or more members selected from the group consisting of these materials and fabrics and so forth. The release sheet of the poultice according to the present invention may be selected from the group consisting of films of polyethylene, polypropylene and polyester; products of release treatment of these films with silicone compounds; release paper and so forth.

The preparation of the poultice will now be described, though the poultice can be easily prepared by known processes.

For example, a nonsteroidal anti-inflammatory agent selected from the group consisting of diclofenac, ketoprofen, flurbiprofen, tenidap, loxoprofen, ketorolac, felbinac, suprofen, indomethacin and ester derivatives and salts of these drugs is solubilized in 3-l-menthoxypropane-1,2-diol to form a solution (A) which may, if necessary, be incorporated with one or more additives selected from the group consisting of a stabilizer, an antioxidant, an ultraviolet absorber, an emulsifying agent, an antiseptic, an antimicrobial and so forth. Separately, a water-soluble polymer is mixed into, dispersed and solubilized in a polyhydric alcohol or water to form a homogeneous paste (B). The solution (A) is added to the paste (B) to form a homogeneous dispersion. This dispersion is spread directly on a support, or alternatively it is once spread on a paper or film treated with a releasing agent and thereafter transferred to a support by pressing. Thus, a poultice according to the present invention is prepared. The above-mentioned procedure for mixing base materials, a drug and other components is just one example, not limiting the procedure for preparing the poultice according to the present invention.

The plaster according to the present invention comprises, for example, (a) a nonsteroidal anti-inflammatory agent selected from the group consisting of diclofenac, ketoprofen, flurbiprofen, tenidap, loxoprofen, ketorolac, felbinac, suprofen and ester derivatives and salts of these drugs, (b) a solubilizer comprising a rosin ester derivative and 3-l-menthoxypropane-1,2-diol, (c) a styrene-isoprene-styrene block copolymer or an acrylic adhesive as the base polymer and (d) a softening agent or a known plaster base.

The support for the plaster is selected from among polypropyene fabrics and polyester fabrics which have no influence on the release of a nonsteroidal anti-inflammatory agent. The polyester fabric to be used as the support is preferably one made of polyethylene terephthalate (PET) or polybutylene terephthalate (PBT). In order to attain excellent release of a nonsteroidal anti-inflammatory agent, it is essential that the support neither interacts with a nonsteroidal anti-inflammatory agent nor adsorb it. From this standpoint, the optimum polymer constituting the support is polypropylene, PET or PBT. The use of a support made of polypropylene, PET or PBT prevents the adsorption of a drug to the support to enable excellent release of the drug.

The plaster according to the present invention is provided with such stretchability that the average stresses at 50% elongation in lengthwise and widthwise directions each is 0.3 kg/cm or below, so that it can be applied to a bend of human skin. By virtue of this stretchability, the plaster according to the present invention not only is capable to be used expediently and to follow the move of the skin so that the friction and pressure during the use of the plaster on the skin decreases, thus causing little side effects such as contact dermatitis.

The plaster according to the present invention is characterized by using a mixture comprising a rosin ester derivative, which is well known by those skilled in the art as a tackifier resin, and 3-l-menthoxypropane-1,2-diol at a specific ratio so as to attain excellent solubility of a drug surprisingly. Further, the use of this mixture improves the release of a drug remarkably. In order to attain more excellent solubility of a drug such as a nonsteroidal anti-inflammatory agent in the base and more excellent release thereof from the base, it is preferable that a nonsteroidal anti-inflammatory agent, a rosin ester derivative and 3-l-menthoxypropane-1,2-diol be contained at a weight ratio of 1:(2 to 25):(1 to 10). When these components are contained at such a ratio as above, the drug exhibits high solubility and releasability.

The term "rosin ester derivative" used in this specification refers to any of the products prepared by esterifying various rosins and subjecting the obtained esters to hydrogenation or purification. The esters include methyl ester, glycerol ester and pentaerythritol ester. The rosin ester derivatives include Ester Gum A, AA-G, H and HP (trade names, products of Arakawa Chemical Industry Co, LTD.), Hariester-L, S and P (trade names, products of Harima Chemicals, Inc.), Super Ester A-75 (trade name, a product of Arakawa Chemical Industry Co., Ltd.), KE-311 (trade name, a product of Arakawa Chemical Industry Co., Ltd.), Hercolyn D (trade name, a product of Hercules Inc.) and Foral 85 and 105 (trade names, products of Hercules Inc.).

The base polymer of the plaster may be selected from conventional ones in consideration of safety For the skin, releasability of a drug and adhesion to the skin. From the standpoint of the release characteristics of a nonsteroidal anti-inflammatory agent, it is preferable that the base polymer be a styrene-isoprene-styrene block copolymer having a particularly low polarity. Such block copolymers include Cariflex TR-1107, TR-1111, TR-1112 and TR-1117 (trade names, products of Shell Chemical) and Solprene 428 (trade name, a product of Phillips Petroleum). These styrene-isoprene-styrene block copolymers may be each used together with other polymer such as polyisobutylene. Vistanex (trade name, a product of Exxon Kagaku) is preferably used as the polyisobutylene.

The softening agent serves to plasticize or soften the styrene-isoprene-styrene block copolymer used as the base polymer to keep the adhesion of the plaster to the skin at a proper level. The softening agent may be selected from the group consisting of almond oil, olive oil, camellia oil, persic oil, peanut oil, liquid paraffin and so forth. The amount of the softening agent used is preferably 150 to 350 parts by weight per 100 parts by weight of the styrene-isoprene-styrene block copolymer.

The content of a drug is preferably 70 to 1200 $\mu g/cm^2$ from the standpoints of therapeutically effective release of a drug and availability thereof, though it is not particularly limited. Preferable proportions of a drug, rosin ester derivative, 3-l-menthoxypropane-1,2-diol, styrene-isoprene-styrene block copolymer and softening agent are as follows.

That is, the plaster comprises 0.5 to 10% by weight of a drug, 5 to 70% by weight of a rosin ester derivative, 0.5 to 10% by weight of 3-l-menthoxypropane-1,2-diol, 5 to 40% by weight of a styrene-isoprene-styrene block copolymer and 10 to 75% by weight of a softening agent, each percentage being based on the total amount.

The plaster according to the present invention can be easily prepared by known processes. For example, it can be prepared by mixing a styrene-isoprene-styrene block copolymer with a softening agent and a rosin ester derivative under heating at 120° to 160° C. by the use of a mixing machine such as kneader or mixer, adding a drug and 3-l-menthoxypropane-1,2-diol to the obtained mixture, and applying the resulting mixture to a support either by spreading the mixture directly on a woven or nonwoven fabric of polypropylene or polyester or by spreading the mixture on a paper or film treated with a releasing agent and thereafter transferring the spread mixture to a desired support by pressing.

Now, brief description will be made of other percutaneously absorbable preparations (such as ointment, gel, cream, gel-type cream, lotion, reserver-type patch, liniment and aerosol) according to the present invention.

The ointment according to the present invention comprises at least higher fatty acid such as myristic acid or an ester thereof, a wax such as spermaceti, a surfactant such as polyoxyethylene and a hydrocarbon such as hydrophilic vaseline in addition to a drug and 3-l-menthoxypropane-1,2-diol.

The ointment can be prepared by, for example, mixing 5 to 15% by weight of a higher fatty acid or an ester thereof with 1 to 10% by weight of a surfactant, 0.5 to 10% by weight of a drug and 0.5 to 10% by weight of 3-l-menthoxypropane-1,2-diol either at room temperature or under heating, adding 4 to 10% by weight of a wax and 50 to 90% by weight of a hydrocarbon to the obtained mixture, heating or heat-melting the resulting mixture, keeping the mixture at 50° to 100° C. to make the whole mixture a transparent solution, homogenating the solution with a homomixer, and lowering the temperature of the resulting solution to room temperature under stirring.

The gel according to the present invention comprises at least a lower alcohol (such as ethanol), water, a gelling agent (such as carboxyvinyl polymer) and a neutralizing agent (such as triethanolamine) in addition to a drug and 3-l-menthoxypropane-1,2-diol.

The gel can be prepared, for example, as follows: 0.5 to 5% by weight of a gelling agent is swollen with at most 55% by weight of water; separately, 0.5 to 10% by weight of a drug is solubilized in 0.5 to 10% by weight of 3-l-menthoxypropane-1,2-diol and the obtained solution is further solubilized in a mixture comprising at most 40% by weight of a glycol and at most 60% by weight of a lower alcohol; the obtained solution is mixed with the gelling agent swollen above; and the resulting mixture is adjusted to pH 4–7 by the addition of a neutralizing agent, thus forming a gel according to the present invention.

The cream according to the present invention comprises at least a higher fatty acid ester such as a myristate, water, a hydrocarbon such as liquid paraffin) and an emulsifying agent such as polyoxyethylene alkyl ether in addition to a drug and 3-l-menthoxypropane-1,2-diol.

The cream can be prepared by stirring a mixture comprising a drug, 3-l-menthoxypropane-1,2-diol, a higher fatty acid ester, water, a hydrocarbon and an emulsifying agent in proper amounts.

A gel-type cream has intermediate properties between a gel and a cream and can be prepared by adding a gelling agent such as a carboxyvinyl polymer to components of cream as described above and adjusting the resulting mixture to pH 4–8, preferably pH 5–6.5 by the addition of a neutralizing agent such as diisopropanolamine.

The gel-type cream according to the present invention can be prepared, for example, as follows: 0.5 to 10% by weight of a drug is solubilized in 0.5 to 10% by weight of 3-l-menthoxypropane-1,2-diol and the obtained solution is further solubilized in a mixture comprising at most 25% by weight of a higher fatty acid ester and at most 40% by weight of a lower alcohol, followed by the addition of at most 5% by weight of an emulsifying agent; separately, 0.5 to 5% by weight of a gelling agent is swollen with water; the swollen agent is mixed with the solution prepared above; and the obtained mixture is homogenized with a homomixer and adjusted to pH 4–8 by the addition of a neutralizing agent.

The lotion according to the present invention comprises at least a lower alcohol such as ethanol and water and/or a glycol in addition to a drug and 3-l-menthoxypropane-1,2-diol.

The lotion can be prepared by stirring a mixture comprising a drug, 3-l-menthoxypropane-1,2-diol, a lower alcohol and water and/or a glycol in proper amounts.

The reserver-type patch according to the present invention comprises at least (1) a backing layer, (2) a drug reserving layer, (3) a drug releasing layer and (4) a pressure-sensitive adhesive layer, wherein the base of the drug reserving layer (2) comprises one mixture selected from the group consisting of (a) mixture comprising at least a glycol, a lower alcohol, water and a water-soluble polymer, (b) a mixture comprising at least an aliphatic alcohol and a polyhydric alcohol and (c) a mixture comprising at least a paraffin and a silicon compound, in addition to a drug and 3-l-menthoxypropane-1,2-diol.

The liniment according to the present invention comprises at least an alcohol such as ethanol or polyethylene glycol, water and an ester of fatty acid such as adipic acid or sebacic acid in addition to a drug and 3-l-menthoxypropane-1,2-diol.

The liniment can be prepared by dissolving 0.5 to 10% by weight of a drug in 0.5 to 10% by weight of 3-l-menthoxypropane-1,2-diol and mixing the obtained solution with 10 to 70% by weight of an alcohol, at most 55% by weight of water and at most 60% by weight of a fatty acid ester under stirring.

The aerosol according to the present invention comprises at least a lower alcohol, water and dimethyl ether and/or liquefied petroleum gas in addition to a drug and 3-l-menthoxypropane-1,2-diol, and may further contain an auxiliary drug such as camphor α-tocopherol or menthol as needed.

The aerosol can be prepared by dissolving 0.5 to 10% by weight of a drug in 0.5 to 10% by weight of 3-l-menthoxypropane-1,2-diol, adding a lower alcohol and water to the obtained solution, charging the obtained mixture into an aerosol container and injecting dimethyl ether and/or liquefied petroleum gas as a propellant into the container.

The percutaneously absorbable preparations according to the present invention may further contain various pharmacologically acceptable additives, so far as the object of the present invention is not marred. Examples of such additives include a stabilizer, an antioxidant, a perfume, a filler, an ultraviolet absorber, an antihistamine, an antiseptic, an antimicrobial agent and an absorbefacient.

Then, the pack according to the present invention will be described. The pack according to the present invention is characterized by using 3-l-menthoxypropane-1,2-diol as the solubilizer for a fat-soluble powder used as the pharmaceutically effective ingredient.

The term "fat-soluble powder" used in this specification refers to a powder which is insoluble or difficultly soluble in water, and such a powder includes pharmaceutically effective ingredients and various additives used in the preparation of the pack. In particular, it is preferable that the powder be selected from the group consisting of glycyrrhetinic acid, stearyl glycyrrhetinate, glycyrrhizinic acid, L-ascorbyl stearate, L-ascorbyl palmitate, calciferol, cholecalciferol, pionin and isopropylmethylphenol. The use of 3-l-menthoxypropane-1,2-diol as the solubilizer for a fat-soluble powder as described above enables the stable dissolution of the powder in the base to give an odorless pack imparting comfortable refreshing refrigeration to the skin.

It is preferable that the content of 3-l-menthoxypropane-1,2-diol in the pack be in the range of 0.001 to 5% by weight. When the content is less than 0.001% by weight, no satisfactory solubilizability will be attained, while when it exceeds 5% by weight, the resulting pack will be poor in physical properties and feelings in use.

The dosage form of the pack according to the present invention is not particularly limited, but may be any conventional one selected from the group consisting of face cleasing packs of creamy, clayey and foam types, sheet packs of pressure-sensitive adhesive type and impregnation type, peel-off pack (of film forming type) and so forth. Of course, the pack may further contain a conventional filler, perfume or the like at need.

DESCRIPTION OF PREFERRED EMBODIMENTS

Figure 1:
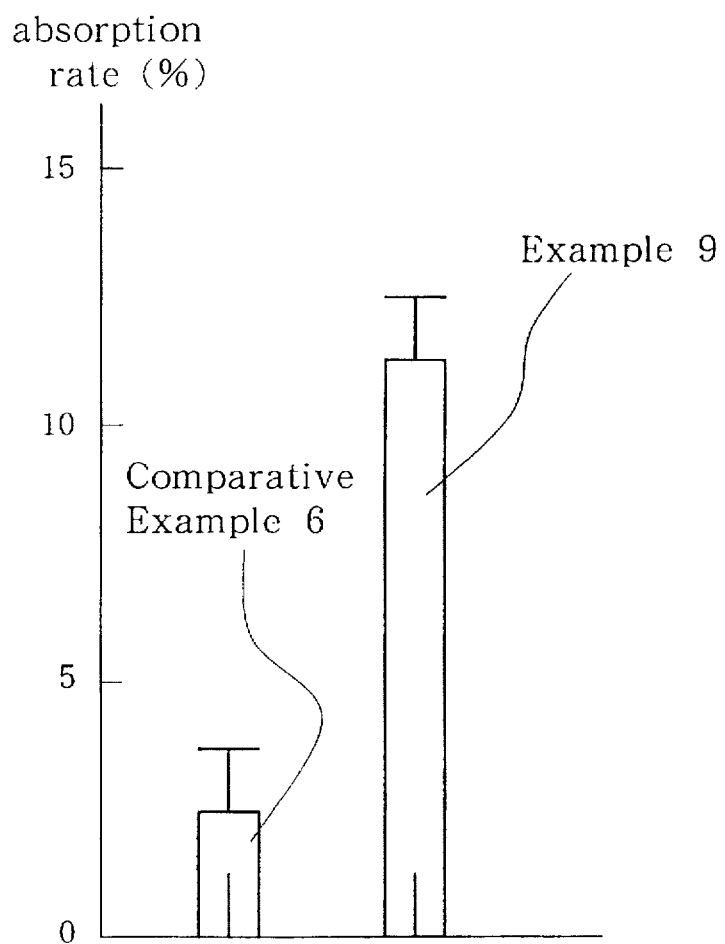
FIGURE 1 is a graph showing the human absorption rates of the plasters of Example 9 and Comparative Example 6.

The present invention will be better understood by Examples which should not be construed as limiting the invention, in comparison with Comparative Examples.

| Example 1 | poultice |
| --- | --- |
| (A) 3-l-menthoxypropane-1,2-diol | 1.0% by weight |
| diclofenac | 0.5% by weight |
| (B) purified water | 48.5% by weight |
| gelatin | 8.0% by weight |
| kaolin | 1.0% by weight |
| glycerol | 35.0% by weight |
| polysodium acrylate | 2.0% by weight |
| polyvinyl alcohol | 3.0% by weight |
| aluminum hydroxide | 1.0% by weight |

The above ingredients were solubilized together and agitated so as to obtain a homogeneous paste. The paste was applied on a polypropylene nonwoven fabric with a speader to obtain a percutaneously absorbable preparation layer having a thickness of 1 mm. Then, the preparation layer was covered with a polypropylene film and cut into pieces each having a predetermined size so as to obtain intended pharmaceutical products.

| Example 2 | poultice |
| --- | --- |
| (A) 3-l-menthoxypropane-1,2-diol | 2.0% by weight |
| loxoprofen | 1.0% by weight |
| thymol | 0.1% by weight |
| (B) purified water | 62.4% by weight |
| gelatin | 3.0% by weight |
| titanium oxide | 1.0% by weight |
| glycerol | 25.0% by weight |
| polysodium acrylate | 3.0% by weight |
| carboxymethyl cellulose | 1.0% by weight |
| ethylene glycol diglycidyl ether | 1.0% by weight |
| sorbitan fatty acid ester | 0.5% by weight |

The above ingredients were solubilized together and agitated so as to obtain a homogeneous paste. The paste was applied on a polyester nonwoven fabric with a spreader to obtain a percutaneously absorbable preparation layer having a thickness of 0.5 mm. Then, the preparation layer was covered with a polyethylene film and cut into pieces each having a predetermined size so as to obtain intended pharmaceutical products.

| Example 3 | poultice |
| --- | --- |
| (A) 3-l-menthoxypropane-1,2-diol | 3.0% by weight |
| ibuprofen | 0.5% by weight |
| ethyl paraben | 0.2% by weight |
| (B) purified water | 42.3% by weight |
| methoxyethylene anhydrous | 5.0% by weight |

| Example 3 | poultice |
| --- | --- |
| maleic acid copolymer | |
| synthetic aluminium silicate | 3.0% by weight |
| glycerol | 40.0% by weight |
| polyacrylic acid | 2.0% by weight |
| polyvinyl alcohol | 2.5% by weight |
| calcium hydroxide | 1.5% by weight |

The above ingredients were solubilized together and agitated so as to obtain a homogeneous paste. The paste was applied on a polyurethane film with a spreader to obtain a percutaneously absorbable preparation layer having a thickness of 1 mm. Then, the preparation layer was covered with a polyurethane film and cut into pieces each having a predetermined size thereby to obtain intended pharmaceutical products.

| Example 4 | poultice |
| --- | --- |
| (A) 3-l-menthoxypropane-1,2-diol | 2.0% by weight |
| ketoprofen | 0.5% by weight |
| (B) purified water | 36.0% by weight |
| N-vinylacetamide | 5.0% by weight |
| glycerol | 50.0% by weight |
| polyacrylic acid | 3.0% by weight |
| carboxymethyl cellulose | 1.0% by weight |
| magnesium metasilicate alminate | 1.5% by weight |
| fatty acid esters of glycerol | 1.0% by weight |

The above ingredients were solubilized together and agitated so as to obtain a homogeneous paste. The paste was applied on a polyester nonwoven fabric with a spreader to obtain a percutaneously absorbable preparation layer having a thickness of 1 mm. Then, the preparation layer was covered with a polyester film and cut into pieces each having a predetermined size so as to obtain intended pharmaceutical products.

| Comparative Example 1 | poultice |
| --- | --- |
| (A) crotamiton | 1.0% by weight |
| suprofen | 0.8% by weight |
| (B) purified water | 54.2% by weight |
| gelatin | 6.0% by weight |
| bentonite | 5.0% by weight |
| glycerol | 25.0% by weight |
| sodium alginate | 2.0% by weight |
| polyethylene oxide | 4.0% by weight |
| aluminum sulfate | 1.5% by weight |
| fatty acid esters of polyethylene glycol | 0.5% by weight |

The above ingredients were solubilized together and agitated thereby to obtain a homogeneous paste. The paste was applied on a polyvinyl chloride with a spreader to obtain a percutaneously absorbable preparation layer having a thickness of 0.3 mm. Then, the preparation layer was covered with a polypropylene film and cut into pieces each having a predetermined size thereby to obtain intended pharmaceutical products.

| Comparative Example 2 | poultice |
| --- | --- |
| (A) glycerol salicylate | 2.0% by weight |
| ketoprofen | 0.5% by weight |
| (B) purified water | 36.0% by weight |

| Comparative Example 2 | poultice |
| --- | --- |
| N-vinylacetamide | 5.0% by weight |
| fatty acid esters of glycerol | 1.0% by weight |
| glycerol | 50.0% by weight |
| polyacrylic acid | 3.0% by weight |
| carboxymethyl cellulose | 1.0% by weight |
| magnesium metasilicate alminate | 1.5% by weight |

The above ingredients were solubilized together and agitated thereby to obtain a homogeneous paste. The paste was applied on a polyester nonwoven fabric with a spreader to obtain a percutaneously absorbable preparation layer having a thickness of 1 mm. Then, the preparation layer was covered with a polyester film and cut into pieces each having a predetermined size thereby to obtain intended pharmaceutical products.

| Comparative Example 3 | poultice |
| --- | --- |
| (A) butylene glycol | 4.0% by weight |
| peppermint oil | 1.0% by weight |
| loxoprofen | 0.5% by weight |
| (B) purified water | 47.5% by weight |
| gelatine | 3.0% by weight |
| kaolin | 1.0% by weight |
| glycerol | 35.0% by weight |
| polysodium acrylate | 3.0% by weight |
| carboxyvinyl polymer | 2.5% by weight |
| dextrin | 2.0% by weight |
| sorbitan polyglycidyl ether | 0.5% by weight |

The above ingredients were solubilized together and agitated thereby to obtain a homogeneous paste. The paste was applied on a polypropylene nonwoven fabric with a spreader to obtain a percutaneously absorbable preparation layer having a thickness of 1 mm. Then, the preparation layer was covered with a polyester film and cut into pieces each having a predetermined size thereby to obtain intended pharmaceutical products.

| Example 5 | plaster |
| --- | --- |
| styrene-isoprene-styrene block copolymer | 22.5% by weight |
| polyisobutylene | 5.0% by weight |
| tackifier (rosin ester) | 15.0% by weight |
| liquid paraffin | 56.0% by weight |
| 3-l-menthoxypropane-1,2-diol | 1.0% by weight |
| ketotifen | 0.5% by weight |

The above components were agitated under heating, thereby obtaining a paste. The paste was spread on a foundation to obtain a tape containing ketotifen.

| Example 6 | plaster |
| --- | --- |
| pressure-sensitive adhesive of acrylic resin solubilizer type (trade name: NISSETSU PE-300) | 77.0% by weight (in terms of solids) |
| 3-l-menthoxypropane-1,2-diol | 15.0% by weight |
| isosorbide dinitrate | 8.0% by weight |

The above components were mixed together to obtain a paste. The paste was spread on a foundation and then freed of the solvent by evaporation thereby to obtain a tape containing isosorbide dinitrate.

| Example 7 | plaster |
| --- | --- |
| silicone adhesive (trade name: BIO-PSA X7-2920) | 89.0% by weight (in terms of solids) |
| 3-l-menthoxypropane-1,2-diol | 7.0% by weight |
| clonidine | 4.0% by weight |

The above components were agitated and mixed together to obtain a paste. The paste was spread on a foundation and then freed of the solvent by evaporation thereby to obtain a tape containing clonidine.

| Comparative Example 4 | plaster |
| --- | --- |
| silicone adhesive (trade name: BIO-PSA X7-2920) | 96.0% by weight (in terms of solids) |
| clonidine | 4.0% by weight |

The above components were mixed together under agitation to obtain a paste. The paste was spread on a foundation and then freed from the solvent by evaporation thereby to obtain a tape containing clonidine. This Comparative Example indicates a formulation which was the same as Example 7 except for 4, 3-l-menthoxypropane-1,2-diol.

| Comparative Example 5 | plaster |
| --- | --- |
| silicone adhesive (trade name: BIO-PSA X7-2920) | 89.0% by weight (in terms of solids) |
| isopropyl myristate | 7.0% by weight |
| clonidine | 4.0% by weight |

The above components were agitated and mixed together to obtain a paste. The paste was spread on a foundation and then freed of the solvent by evaporation thereby to obtain a tape containing clonidine. This Comparative Example 5 indicates a formulation which was the same as Example 7 except that isopropyl myristate was substituted for the menthoxypropane-1,2-diol used in Example 7.

| Example 8 | plaster |
| --- | --- |
| styrene-isoprene-styrene block copolymer (trade name: Cariflex TR-1107) | 25.0% by weight |
| liquid paraffin | 59.0% by weight |
| rosin ester derivative (trade name: Ester Gum AA-G) | 5.0% by weight |
| 3-l-menthoxypropane-1,2-diol | 10.0% by weight |
| diclofenac | 1.0% by weight |

The components of the above prescription were mixed by a kneader to obtain a paste. Thereafter, the paste was applied directly on a PBT woven fabric and then covered with a liner to obtain a plaster.

| Example 9 | plaster |
| --- | --- |
| styrene-isoprene-styrene block copolymer (trade name: Cariflex TR-1107) | 20.0% by weight |
| liquid paraffin | 43.5% by weight |
| polyisobutylene (trade name: Vistanex) | 10.0% by weight |
| rosin ester derivative | 21.5% by weight |

-continued

| Example 9 | plaster |
|---|---|
| (trade name: KE-311) | |
| 3-l-menthoxypropane-1,2-diol | 4.0% by weight |
| diclofenac | 1.0% by weight |

The components of the above prescription were mixed by a mixer to obtain a paste. The paste was applied on a plastic film previously endowed with releasability and then covered with a PET woven fabric and pressure-contact transferred to obtain a plaster.

| Example 10 | plaster |
|---|---|
| styrene-isoprene-styrene block copolymer (trade name: Cariflex TR-1107) | 21.0% by weight |
| liquid paraffin | 63.0% by weight |
| rosin ester derivative (trade name: KE-311) | 10.0% by weight |
| 3-l-menthoxypropane-1,2-diol | 4.0% by weight |
| diclofenac | 2.0% by weight |

The components of the above prescription were mixed together by a kneader to obtain a paste. The paste was applied on a plastic film previously endowed with releasability and, covered tereon with a PBT nonwoven fabric and pressure-contact transferred to obtain a plaster.

| Example 11 | plaster |
|---|---|
| styrene-isoprene-styrene block copolymer (trade name: Cariflex TR-1111) | 30.0% by weight |
| liquid paraffin | 57.0% by weight |
| rosin ester derivative (trade name: Ester Gum H) | 7.0% by weight |
| 3-l-menthoxypropane-1,2-diol | 5.0% by weight |
| diclofenac | 1.0% by weight |

The components of the above prescription were mixed together by a kneader to obtain a paste. The paste was applied on a plastic film previously endowed with releasability, thereon covered with a polypropylene nonwoven fabric and pressure-contact transferred to obtain a plaster.

| Example 12 | plaster |
|---|---|
| styrene-isoprene-styrene block copolymer (trade name: Cariflex TR-1111) | 15.0% by weight |
| polyisobutylene (trade name: Vistanex) | 5.0% by weight |
| liquid paraffin | 23.0% by weight |
| rosin ester derivative (trade name: Ester Gum H) | 42.0% by weight |
| 3-l-menthoxypropane-1,2-diol | 10.0% by weight |
| diclofenac | 5.0% by weight |

The components of the above prescription were mixed together by a kneader to obtain a paste. The paste was applied on a plastic film previously endowed with releasability, thereon covered with a polypropylene nonwoven fabric and pressure-contact transferred to obtain a plaster.

| Example 13 | plaster |
|---|---|
| styrene-isoprene-styrene block copolymer (trade name: Cariflex TR-1112) | 18.0% by weight |
| liquid paraffin | 54.5% by weight |
| rosin ester derivative (trade name: Foral 105) | 18.5% by weight |
| 3-l-menthoxypropane-1,2-diol | 6.0% by weight |
| diclofenac methyl ester | 3.0% by weight |

A plaster was obtained in the same manner as in Example 8.

| Example 14 | plaster |
|---|---|
| styrene-isoprene-styrene block copolymer (trade name: Cariflex TR-1107) | 25.0% by weight |
| liquid paraffin | 68.0% by weight |
| rosin ester derivative (trade name: Ester Gum AA-G) | 5.0% by weight |
| 3-l-menthoxypropane-1,2-diol | 1.5% by weight |
| ketoprofen | 0.5% by weight |

A plaster was obtained in the same manner as in Example 9.

| Example 15 | plaster |
|---|---|
| styrene-isoprene-styrene block copolymer (trade name: Cariflex TR-1107) | 20.0% by weight |
| liquid paraffin | 43.5% by weight |
| rosin ester derivative (trade name: KE-311) | 30.5% by weight |
| 3-l-menthoxypropane-1,2-diol | 3.0% by weight |
| ketoprofen | 3.0% by weight |

A plaster was obtained in the same manner as in Example 10.

| Example 16 | plaster |
|---|---|
| styrene-isoprene-styrene block copolymer (trade name: Cariflex TR-1111) | 15.0% by weight |
| polyisobutene (trade name: Vistanex) | 7.0% by weight |
| liquid paraffin | 23.0% by weight |
| rosin ester derivative (trade name: Ester Gum H) | 40.0% by weight |
| 3-l-menthoxypropane-1,2-diol | 10.0% by weight |
| ketoprofen | 5.0% by weight |

A plaster was obtained in the same manner as in Example 11.

| Example 17 | plaster |
|---|---|
| styrene-isoprene-styrene block copolymer (trade name: Solprene 418) | 28.0% by weight |
| polybutene | 5.0% by weight |
| liquid paraffin | 57.7% by weight |
| rosin ester derivative (trade name: KE-311) | 7.0% by weight |

| Example 17 | plaster |
|---|---|
| 3-l-menthoxypropane-1,2-diol | 1.8% by weight |
| flurbiprofen | 0.5% by weight |

A plaster was obtained in the same manner as in Example 12.

| Example 18 | plaster |
|---|---|
| styrene-isoprene-styrene block copolymer (trade name: Cariflex TR-1107) | 21.0% by weight |
| liquid paraffin | 66.8% by weight |
| rosin ester derivative (trade name: KE-311) | 7.2% by weight |
| 3-l-menthoxypropane-1,2-diol | 4.0% by weight |
| flurbiprofen | 1.0% by weight |

A plaster was obtained in the same manner as in Example 9.

| Example 19 | plaster |
|---|---|
| styrene-isoprene-styrene block copolymer (trade name: Cariflex TR-1107) | 21.0% by weight |
| liquid paraffin | 45.0% by weight |
| rosin ester derivative (trade name: KE-311) | 20.0% by weight |
| 3-l-menthoxypropane-1,2-diol | 9.0% by weight |
| flurbiprofen | 5.0% by weight |

A plaster was obtained in the same manner as in Example 10.

| Example 20 | plaster |
|---|---|
| styrene-isoprene-styrene block copolymer (trade name: Cariflex TR-1107) | 11.0% by weight |
| styrene-isoprene-styrene block copolymer (trade name: Cariflex TR-1111) | 11.0% by weight |
| liquid paraffin | 44.0% by weight |
| rosin ester derivative (trade name: Ester Gum AA-G) | 26.0% by weight |
| 3-l-menthoxypropane-1,2-diol | 7.0% by weight |
| flurbiprofen | 1.0% by weight |

A plaster was obtained in the same manner as in Example 12.

| Example 21 | plaster |
|---|---|
| styrene-isoprene-styrene block copolymer (trade name: Cariflex TR-1107) | 30.0% by weight |
| liquid paraffin | 56.0% by weight |
| rosin ester derivative (trade name: KE-311) | 8.0% by weight |
| 3-l-menthoxypropane-1,2-diol | 5.0% by weight |
| loxoprofen | 1.0% by weight |

A plaster was obtained in the same manner as in Example 11.

| Example 22 | plaster |
|---|---|
| styrene-isoprene-styrene block copolymer (trade name: Cariflex TR-1111) | 12.0% by weight |
| liquid paraffin | 28.0% by weight |
| rosin ester derivative (trade name: Ester Gum H) | 40.0% by weight |
| 3-l-menthoxypropane-1,2-diol | 12.0% by weight |
| loxoprofen | 8.0% by weight |

A plaster was obtained in the same manner as in Example 11.

| Example 23 | plaster |
|---|---|
| styrene-isoprene-styrene block copolymer (trade name: Cariflex TR-1112) | 21.0% by weight |
| liquid paraffin | 50.0% by weight |
| rosin ester derivative (trade name: Ester Gum H) | 20.5% by weight |
| 3-l-menthoxypropane-1,2-diol | 5.5% by weight |
| loxoprofen | 3.0% by weight |

A plaster was obtained in the same manner as in Example 12.

| Example 24 | plaster |
|---|---|
| styrene-isoprene-styrene block copolymer (trade name: Cariflex TR-1111) | 10.0% by weight |
| liquid paraffin | 43.0% by weight |
| rosin ester derivative (trade name: KE-311) | 35.0% by weight |
| 3-l-menthoxypropane-1,2-diol | 10.0% by weight |
| sodium loxoprofen | 2.0% by weight |

A plaster was obtained in the same manner as in Example 9.

| Example 25 | plaster |
|---|---|
| styrene-isoprene-styrene block copolymer (trade name: Cariflex TR-1107) | 20.0% by weight |
| liquid paraffin | 47.0% by weight |
| rosin ester derivative (trade name: Ester Gum H) | 21.0% by weight |
| 3-l-menthoxypropane-1,2-diol | 9.0% by weight |
| sodium loxoprofen | 3.0% by weight |

A plaster was obtained in the same manner as in Example 10.

| Example 26 | plaster |
|---|---|
| styrene-isoprene-styrene block copolymer (trade name: Cariflex TR-1107) | 22.0% by weight |
| polyisobutylene (trade name: Vistanex) | 5.0% by weight |
| liquid paraffin | 52.0% by weight |
| rosin ester derivative (trade name: Hercolyn D) | 12.0% by weight |

| Example 26 | plaster |
|---|---|
| 3-l-menthoxypropane-1,2-diol | 7.0% by weight |
| loxoprofen | 2.0% by weight |

A plaster was obtained in the same manner as in Example 11.

| Example 27 | plaster |
|---|---|
| styrene-isoprene-styrene block copolymer (trade name: Cariflex TR-1111) | 20.0% by weight |
| liquid paraffin | 38.0% by weight |
| rosin ester derivative (trade name: KE-311) | 30.0% by weight |
| 3-l-menthoxypropane-1,2-diol | 8.0% by weight |
| ketorolac | 4.0% by weight |

A plaster was obtained in the same manner as in Example 9.

| Example 28 | plaster |
|---|---|
| styrene-isoprene-styrene block copolymer (trade name: Cariflex TR-1107) | 28.0% by weight |
| liquid paraffin | 57.5% by weight |
| rosin ester derivative (trade name: Ester Gum H) | 9.0% by weight |
| 3-l-menthoxypropane-1,2-diol | 4.5% by weight |
| ketorolac | 1.0% by weight |

A plaster was obtained in the same manner as in Example 11.

| Example 29 | plaster |
|---|---|
| styrene-isoprene-styrene block copolymer (trade name: Cariflex TR-1112) | 21.0% by weight |
| liquid paraffin | 53.0% by weight |
| rosin ester derivative (trade name: Ester Gum H) | 10.0% by weight |
| 3-l-menthoxypropane-1,2-diol | 14.0% by weight |
| ketorolac tromethamine | 2.0% by weight |

A plaster was obtained in the same manner as in Example 12.

| Example 30 | plaster |
|---|---|
| styrene-isoprene-styrene block copolymer (trade name: Cariflex TR-1111) | 33.0% by weight |
| liquid paraffin | 60.0% by weight |
| rosin ester derivative (trade name: Foral 105) | 5.0% by weight |
| 3-l-menthoxypropane-2,2-diol | 1.5% by weight |
| ketorolac | 0.5% by weight |

A plaster was obtained in the same manner as in Example 11.

| Example 31 | plaster |
|---|---|
| styrene-isoprene-styrene block copolymer (trade name: Cariflex TR-1111) | 20.0% by weight |
| polyisobutylene (trade name: Vistanex) | 5.0% by weight |
| liquid paraffin | 55.0% by weight |
| rosin ester derivative (trade name: KE-311) | 10.0% by weight |
| 3-l-menthoxypropane-1,2-diol | 8.0% by weight |
| ketoprofen | 2.0% by weight |

A plaster was obtained in the same manner as in Example 8.

| Example 32 | plaster |
|---|---|
| styrene-isoprene-styrene block copolymer (trade name: Cariflex TR-1111) | 15.0% by weight |
| polyisobutylene (trade name: Vistanex) | 14.0% by weight |
| liquid paraffin | 38.0% by weight |
| rosin ester derivative (trade name: KE-311) | 25.0% by weight |
| 3-l-menthoxypropane-1,2-dioi | 5.0% by weight |
| ketoprofen | 3.0% by weight |

A plaster was obtained in the same manner as in Example 9.

| Example 33 | plaster |
|---|---|
| styrene-isoprene-styrene block copolymer (trade name: Cariflex TR-1111) | 22.0% by weight |
| polyisobutylene (trade name: Vistanex) | 8.0% by weight |
| liquid paraffin | 48.0% by weight |
| rosin ester derivative (trade name: KE-311) | 14.0% by weight |
| 3-l-menthoxypropane-1,2-diol | 8.0% by weight |
| ketorolac | 2.0% by weight |

A plaster was obtained in the same manner as in Example 10.

| Example 34 | plaster |
|---|---|
| styrene-isoprene-styrene block copolymer (trade name: Cariflex TR-1111) | 15.0% by weight |
| polyisobutylene (trade name: Vistanex) | 12.0% by weight |
| liquid paraffin | 27.0% by weight |
| rosin ester derivative (trade name: KE-311) | 38.0% by weight |
| 3-l-menthoxypropane-1,2-diol | 4.0% by weight |
| ketorolac | 4.0% by weight |

A plaster was obtained in the same manner as in Example 10.

| Example 35 | plaster |
|---|---|
| styrene-isoprene-styrene block copolymer | 20.0% by weight |

| Example 35 | plaster |
|---|---|
| (trade name: Cariflex TR-1107) | |
| liquid paraffin | 45.5% by weight |
| rosin ester derivative | 30.5% by weight |
| (trade name: KE-311) | |
| 3-l-menthoxypropane-1,2-diol | 3.0% by weight |
| felbinac | 1.0% by weight |

A plaster was obtained in the same manner as in Example 10.

| Example 36 | plaster |
|---|---|
| styrene-isoprene-styrene block copolymer | 15.0% by weight |
| (trade name: Cariflex TR-1111) | |
| polyisobutylene | 14.0% by weight |
| (trade name: Vistanex) | |
| liquid paraffin | 38.0% by weight |
| rosin ester derivative | 26.0% by weight |
| (trade name: KE-311) | |
| 3-l-menthoxypropane-1,2-diol | 5.0% by weight |
| felbinac | 2.0% by weight |

A plaster was obtained in the same manner as in Example 12.

| Example 37 | plaster |
|---|---|
| styrene-isoprene-styrene block copolymer | 22.0% by weight |
| (trade name: Cariflex TR-1107) | |
| polyisobutylene | 5.0% by weight |
| (trade name: Vistanex) | |
| liquid paraffin | 52.0% by weight |
| rosin ester derivative | 12.0% by weight |
| (trade name: Hercolyn D) | |
| 3-l-menthoxypropane-1,2-diol | 7.0% by weight |
| felbinac | 2.0% by weight |

A plaster was obtained in the same manner as in Example 11.

| Example 38 | plaster |
|---|---|
| styrene-isoprene-styrene block copolymer | 28.0% by weight |
| (trade name: Solprene 418) | |
| polybutene | 5.0% by weight |
| liquid paraffin | 57.0% by weight |
| rosin ester derivative | 7.5% by weight |
| (trade name: KE-311) | |
| 3-l-menthoxypropane-1,2-diol | 2.0% by weight |
| suprofen | 0.5% by weight |

A plaster was obtained in the same manner as in Example 12.

| Example 39 | plaster |
|---|---|
| styrene-isoprene-styrene block copolymer | 20.0% by weight |
| (trade name: Cariflex TR-1111) | |
| liquid paraffin | 40.0% by weight |
| rosin ester derivative | 34.0% by weight |
| (trade name: KE-311) | |
| 3-l-menthoxypropane-1,2-diol | 4.0% by weight |
| suprofen | 2.0% by weight |

A plaster was obtained in the same manner as in Example 9.

| Example 40 | plaster |
|---|---|
| styrene-isoprene-styrene block copolymer | 20.0% by weight |
| (trade name: Cariflex TR-1107) | |
| polyisobutylene | 5.0% by weight |
| (trade name: Vistanex) | |
| liquid paraffin | 45.0% by weight |
| rosin ester derivative | 20.0% by weight |
| (trade name: KE-311) | |
| 3-l-menthoxypropane-1,2-diol | 9.0% by weight |
| estradiol | 1.0% by weight |

A plaster was obtained in the same manner as in Example 8.

| Example 41 | plaster |
|---|---|
| styrene-isoprene-styrene block copolymer | 20.0% by weight |
| (trade name: Cariflex TR-1111) | |
| polyisobutylene | 12.0% by weight |
| (trade name: Vistanex) | |
| liquid paraffin | 37.0% by weight |
| rosin ester derivative | 20.0% by weight |
| (trade name: Ester Gum H) | |
| 3-l-menthoxypropane-1,2-diol | 10.0% by weight |
| estradiol | 1.0% by weight |

A plaster was obtained in the same manner as in Example 9.

| Example 42 | plaster |
|---|---|
| styrene-isoprene-styrene block copolymer | 22.0% by weight |
| (trade name: Cariflex TR-1111) | |
| polyisobutylene | 6.0% by weight |
| (trade name: Vistanex) | |
| liquid paraffin | 45.0% by weight |
| rosin ester derivative | 23.0% by weight |
| (trade name: Foral 105) | |
| 3-l-menthoxypropane-1,2-diol | 3.0% by weight |
| progesterone | 1.0% by weight |

A plaster was obtained in the same manner as in Example 10.

| Example 43 | plaster |
|---|---|
| styrene-isoprene-styrene block copolymer | 15.0% by weight |
| (trade name: Cariflex TR-1107) | |
| polyisobutylene | 10.0% by weight |
| (trade name: Vistanex) | |
| liquid paraffin | 39.0% by weight |
| rosin ester derivative | 30.0% by weight |
| (trade name: KE-311) | |

| Example 43 | plaster |
|---|---|
| 3-l-menthoxypropane-1,2-diol | 5.0% by weight |
| progesterone | 1.0% by weight |

A plaster was obtained in the same manner as in Example 11.

| Example 44 | plaster |
|---|---|
| styrene-isoprene-styrene block copolymer (trade name: Cariflex TR-1111) | 20.0% by weight |
| polyisobutylene (trade name: Vistanex) | 5.0% by weight |
| liquid paraffin | 47.0% by weight |
| rosin ester derivative (trade name: KE-311) | 17.0% by weight |
| 3-l-menthoxypropane-1,2-diol | 10.0% by weight |
| norethisterone | 1.0% by weight |

A plaster was obtained in the same manner as in Example 12.

| Example 45 | plaster |
|---|---|
| styrene-isoprene-styrene block copolymer (trade name: Cariflex TR-1111) | 20.0% by weight |
| polyisobutylene (trade name: Vistanex) | 11.0% by weight |
| liquid paraffin | 25.0% by weight |
| rosin ester derivative (trade name: Ester Gum H) | 30.0% by weight |
| 3-l-menthoxypropane-1,2-diol | 13.0% by weight |
| norethisterone | 1.0% by weight |

A plaster was obtained in the same manner as in Example 10.

| Example 46 | plaster |
|---|---|
| styrene-isoprene-styrene block copolymer (trade name: Cariflex TR-1112) | 20.0% by weight |
| polyisobutylene (trade name: Vistanex) | 12.0% by weight |
| liquid paraffin | 30.0% by weight |
| rosin ester derivative (trade name: Foral 105) | 30.0% by weight |
| 3-l-menthoxypropane-1,2-diol | 7.0% by weight |
| testosterone | 1.0% by weight |

A plaster was obtained in the same manner as in Example 9.

| Example 47 | plaster |
|---|---|
| styrene-isoprene-styrene block copolymer (trade name: Cariflex TR-1107) | 22.0% by weight |
| polyisobutylene (trade name: Vistanex) | 5.0% by weight |
| liquid paraffin | 45.0% by weight |
| rosin ester derivative (trade name: KE-311) | 22.0% by weight |
| 3-l-menthoxypropane-1,2-diol | 5.0% by weight |
| testosterone | 1.0% by weight |

A plaster was obtained in the same manner as in Example 12.

| Comparative Example 6 | plaster |
|---|---|
| styrene-isoprene-styrene block copolymer (trade name: Cariflex TR-1107) | 20.0% by weight |
| liquid paraffin | 43.5% by weight |
| polyisobutylene (trade name: Vistanex) | 10.0% by weight |
| rosin ester derivative (trade name: KE-311) | 21.5% by weight |
| diclofenac | 1.0% by weight |

The components of the above prescription were mixed by a mixer to obtain a paste. The paste was applied on a plastic film previously endowed with releasability, thereon covered with polyester fabric and pressure-contact transferred to obtain a plaster. The prescription of Comparative Example 6 was the same as that of Example 9 except that the former lacked in 3-l-menthoxy propane-1,2-diol as a solubilizer.

| Example 48 | ointment |
|---|---|
| white vaseline | 76.0% by weight |
| glycerol monostearate | 10.0% by weight |
| beef tallow | 10.0% by weight |
| silicone oil | 1.0% by weight |
| 3-l-menthoxypropane-1,2-diol | 2.0% by weight |
| flurbiprofen | 1.0% by weight |

The above components were mixed together under agitation, thereby to prepare an ointment comprising flurbiprofen.

| Example 49 | ointment |
|---|---|
| white vaseline | 76.95% by weight |
| diethyl sebacate | 5.0% by weight |
| spermaceti | 5.0% by weight |
| sodium polyoxyethylene-lauryletherphosphate | 4.0% by weight |
| 2-hydroxy-4-methoxybenzophenone | 1.0% by weight |
| butyl p-oxybenzoate | 0.05% by weight |
| 3-l-menthoxypropane-1,2-diol | 5.0% by weight |
| ketoprofen | 3.0% by weight |

The above components were mixed together under agitation, thereby to prepare an ointment comprising ketoprofen.

| Example 50 | ointment |
|---|---|
| white vaseline | 82.95% by weight |
| isopropyl myristate | 8.0% by weight |
| spermaceti | 3.0% by weight |
| sodium polyoxyethylene-lauryletherphosphate | 2.0% by weight |
| butyl p-oxybenzoate | 0.05% by weight |

| Example 50 | ointment |
|---|---|
| 3-l-menthoxypropane-1,2-diol | 3.0% by weight |
| indomethacin | 1.0% by weight |

The above components were mixed together under agitation, thereby to prepare an ointment comprising indomethacin.

| Example 51 | gel |
|---|---|
| carboxyvinyl polymer | 2.0% by weight |
| hydroxypropylcellulose | 2.0% by weight |
| ethanol | 37.0% by weight |
| purified water | 33.0% by weight |
| propylene glycol | 15.0% by weight |
| diisopropyladipate | 2.0% by weight |
| diisopropanolamine | 2.5% by weight |
| 2-hydroxy-4-methoxybenzophenone | 0.5% by weight |
| 3-l-menthoxypropane-1,2-diol | 3.0% by weight |
| ketoprofen | 3.0% by weight |

The above components were mixed together under agitation, thereby to prepare a gel comprising ketoprofen.

| Example 52 | gel |
|---|---|
| carboxyvinyl polymer | 1.5% by weight |
| hydroxypropylcellulose | 2.0% by weight |
| ethanol | 17.0% by weight |
| purified water | 35.3% by weight |
| propylene glycol | 30.0% by weight |
| propylene carbonate | 10.0% by weight |
| triethanolamine | 0.2% by weight |
| 3-l-menthoxypropane-1,2-diol | 3.0% by weight |
| indomethacin | 1.0% by weight |

The above components were mixed together under agitation, thereby to prepare a gel comprising indomethacin.

| Example 53 | gel |
|---|---|
| carboxyvinyl polymer | 1.0% by weight |
| ethanol | 35.0% by weight |
| purified water | 49.0% by weight |
| propylene glycol | 10.0% by weight |
| diisopropanolamine | 1.0% by weight |
| 3-l-menthoxypropane-1,2-diol | 3.0% by weight |
| flurbiprofen | 1.0% by weight |

The above components were mixed together under agitation, thereby to prepare a gel comprising flurbiprofen.

| Example 54 | cream |
|---|---|
| liquid paraffin | 10.0% by weight |
| middle chain triacylglycerol | 5.0% by weight |
| polyethylene glycol monostearate | 3.0% by weight |
| glycerol | 5.0% by weight |
| carboxyvinyl polymer | 1.0% by weight |
| diisopropanolamine | 0.4% by weight |
| methyl p-oxybenzoate | 0.2% by weight |
| indomethacin | 1.0% by weight |
| 3-l-menthoxypropane-1,2-diol | 5.0% by weight |
| purified water | residual quantity |

The above components were mixed together under agitation, thereby to prepare a cream comprising indomethacin.

| Example 55 | cream |
|---|---|
| carboxyvinyl polymer | 1.0% by weight |
| isopropyl myristate | 5.0% by weight |
| ethanol | 5.0% by weight |
| polyethylene glycol monostearate | 1.0% by weight |
| coconut oil fatty acid diethanolamide | 3.0% by weight |
| methyl p-oxybenzoate | 0.2% by weight |
| 2-hydroxy-4-methoxybenzophenone | 0.8% by weight |
| ketoprofen | 3.0% by weight |
| 3-l-menthoxypropane-1,2-diol | 7.0% by weight |
| purified water | residual quantity |

The above components were mixed together under agitation, thereby to prepare a cream comprising ketoprofen.

| Example 56 | cream |
|---|---|
| carboxyvinyl polymer | 1.0% by weight |
| glycerol | 10.0% by weight |
| ethanol | 5.0% by weight |
| diisopropanolamine | 0.4% by weight |
| medium chain triglyceride | 3.0% by weight |
| flurbiprofen | 1.0% by weight |
| 3-l-menthoxypropane-1,2-diol | 5.0% by weight |
| purified water | residual quantity |

The above components were mixed together under agitation, thereby to prepare a cream comprising flurbiprofen.

| Example 57 | gel-type cream |
|---|---|
| carboxyvinyl polymer | 1.0% by weight |
| isopropyl myristate | 10.0% by weight |
| ethanol | 5.0% by weight |
| polyethyleneglycol monostearate | 1.0% by weight |
| methyl p-oxybenzoate | 0.2% by weight |
| coconut oil fatty acid diethanolamide | 3.0% by weight |
| ketoprofen | 3.0% by weight |
| 3-l-menthoxypropane-1,2-diol | 3.0% by weight |
| purified water | residual quantity |

The above components were mixed together under agitation, thereby to prepare a gel-type cream comprising ketoprofen.

| Example 58 | gel-type cream |
|---|---|
| carboxyvinyl polymer | 1.0% by weight |
| isopropyl palmitate | 9.0% by weight |
| diethyl sebacate | 9.0% by weight |
| polyoxyethylene cetylether | 2.0% by weight |
| propylene carbonate | 7.0% by weight |
| methyl p-oxybenzoate | 0.2% by weight |
| sodium hydroxide | 0.1% by weight |
| indomethacin | 1.0% by weight |
| 3-l-menthoxypropane-1,2-diol | 5.0% by weight |
| purified water | residual quantity |

The above components were mixed together under agitation, thereby to prepare a gel-type cream comprising indomethacin.

| Example 59 | gel-type cream |
|---|---|
| carboxyvinyl polymer | 1.5% by weight |
| cetyl isooctanoate | 10.0% by weight |
| ethanol | 5.0% by weight |
| polyethyleneglycol monostearate | 1.0% by weight |
| methyl p-oxybenzoate | 0.2% by weight |
| coconut oil fatty acid diethanolamide | 3.0% by weight |
| flurbiprofen | 3.0% by weight |
| 3-l-menthoxypropane-1,2-diol | 5.0% by weight |
| purified water | residual quantity |

The above components were mixed together under agitation, thereby to prepare a gel-type cream comprising flurbiprofen.

| Example 60 | gel-type cream |
|---|---|
| carboxyvinyl polymer | 1.0% by weight |
| isopropyl myristate | 6.0% by weight |
| diethyl sebacate | 5.0% by weight |
| polyoxyethylene cethylether | 2.0% by weight |
| propylene carbonate | 3.0% by weight |
| methyl p-oxybenzoate | 0.2% by weight |
| sodium hydroxide | 0.1% by weight |
| ketorolac | 3.0% by weight |
| 3-l-menthoxypropane-1,2-diol | 7.0% by weight |
| purified water | residual quantity |

The above components were mixed together under agitation, thereby to prepare a gel-type cream comprising ketorolac.

| Example 61 | lotion |
|---|---|
| ethanol | 57.0% by weight |
| purified water | 34.0% by weight |
| propylene glycol | 5.0% by weight |
| 3-l-menthoxypropane-1,2-diol | 3.0% by weight |
| ketoprofen | 1.0% by weight |

The above components were mixed together under agitation, thereby to prepare a lotion comprising ketoprofen.

| Example 62 | lotion |
|---|---|
| ethanol | 38.0% by weight |
| purified water | 50.0% by weight |
| propylene glycol | 6.0% by weight |
| 3-l-menthoxypropane-1,2-diol | 5.0% by weight |
| indomethacin | 1.0% by weight |

The above components were mixed together under agitation, thereby to prepare a lotion comprising indomethacin.

| Example 63 | lotion |
|---|---|
| ethanol | 30.0% by weight |
| purified water | 50.2% by weight |
| propylene glycol | 10.0% by weight |
| methylcellulose | 0.8% by weight |
| 3-l-menthoxypropane-1,2-diol | 7.0% by weight |
| flurbiprofen | 2.0% by weight |

The above components were mixed together under agitation, thereby to prepare a lotion comprising flurbiprofen.

| Example 64 | reserver-type patch |
|---|---|
| (1) a backing layer | polyester-type film |
| (2) a drug reserving layer | 4 g of the following gel components were enclosed in the drug reserving layer. |
| ketorolac | 5.0% by weight |
| 3-l-menthoxypropane-1,2-diol | 3.0% by weight |
| carboxyvinyl polymer | 2.0% by weight |
| propylene glycol | 30.0% by weight |
| triethyl citrate | 19.0% by weight |
| purified water | 39.4% by weight |
| 2-hydroxy-4-methoxybenzophenone | 0.5% by weight |
| diisopropanolamine | 1.1% by weight |
| (3) a drug releasing layer | Juragard (trade name, a product of Polyplastic Co., Ltd.) |
| (4) a pressure-sensitive adhesive layer | silicon-type adhesive |

This reserver-type patch consisted of the above (1)–(4) layers and a releasing liner was put on the pressure-sensitive adhesive surface thereby to obtain a laminate.

| Example 65 | reserver-type patch |
|---|---|
| (1) a backing layer | polyester-type film |
| (2) a drug reserving layer | 4 g of the following gel composition were enclosed in the drug reserving layer. |
| ketoprofen | 3.0% by weight |
| 3-l-menthoxypropane-1,2-diol | 5.0% by weight |
| liquid paraffin | 70.0% by weight |
| stearyl alcohol | 20.0% by weight |
| d-limonene | 2.0% by weight |
| (3) a drug releasing layer | Cotran (tradename, a product of 3M Co., Ltd. |
| (4) a pressure-sensitive adhesive layer | polyisobutylene-type adhesive |

This reserver-type patch consisted of the above (1)–(4) layers and a releasing liner was put on the pressure-sensitive adhesive surface thereby to obtain a laminate.

| Example 66 | reserver-type patch |
|---|---|
| (1) a backing layer | Aluminum laminating polyester film |
| (2) a drug reserving layer | 4 g of the following gel composition were enclosed in the drug reserving layer. |
| ketorolac | 5.0% by weight |
| 3-l-menthoxypropane-1,2-diol | 10.0% by weight |
| silicon | 80.0% by weight |
| glycerol monolaurate | 5.0% by weight |
| (3) a drug releasing layer | Cotran |
| (4) a pressure-sensitive adhesive layer | silicon-type adhesive (around a support) |

This reserver-type patch consisted of the above (1)–(4) layers and a releasing liner was put on the pressure-sensitive adhesive surface thereby to obtain a laminate.

| Example 67 | reserver-type patch |
|---|---|
| (1) a backing layer | Aluminum laminating polyester film |
| (2) a drug reserving layer | 4 g of the following gel composition were enclosed in the drug reserving layer. |
| ketorolac | 5.0% by weight |
| 3-l-menthoxypropane-1,2-diol | 10.0% by weight |
| silicon | 80.0% by weight |
| glycerol monolauric acid | 5.0% by weight |
| (3) a drug releasing layer | Cotran |
| (4) a pressure-sensitive adhesive layer | silicon-type adhesive (around a support) |

This reserver-type patch consisted of the above (1)–(4) layers and a releasing liner was put on the pressure-sensitive adhesive surface to obtain a laminate.

| Example 68 | reserver-type patch |
|---|---|
| (1) a backing layer | Aluminum laminating polyester film |
| (2) a drug reserving layer | 4 g of the following gel composition were enclosed in the drug reserving layer. |
| tulobuterol hydrochloride | 5.0% by weight |
| 3-l-menthoxypropane-1,2-diol | 5.0% by weight |
| stearyl alcohol | 10.0% by weight |
| cetyl alcohol | 10.0% by weight |
| behenyl alcohol | 10.0% by weight |
| propylene glycol | 20.0% by weight |
| 1,3-butylene glycol | 35.0% by weight |
| lauryl alcohol | 5.0% by weight |
| (3) a drug releasing layer | Cotran |
| (4) a pressure-sensitive adhesive layer | silicon-type adhesive (around a support) |

This reserver-type patch consisted of the above (1)–(4) layers and a releasing liner was put on the pressure-sensitive adhesive surface to obtain a laminate.

| Example 69 | liniment |
|---|---|
| ethanol | 45.0% by weight |
| 2-hydroxy-4-methoxybenzophenone | 0.6% by weight |
| diisopropyl adipate | 30.0% by weight |
| α-tocopherol | 1.0% by weight |
| hydroxypropylcellulose | 1.5% by weight |
| ketoprofen | 2.0% by weight |
| 3-l-menthoxypropane-1,2-diol | 4.0% by weight |
| purified water | 15.9% by weight |

The above components were mixed together under agitation, thereby to prepare a lotion comprising ketoprofen.

| Example 70 | liniment |
|---|---|
| propyleneglycol | 10.0% by weight |
| 2-hydroxy-4-methoxybenzophenone | 0.2% by weight |
| polyethyleneglycol monolaurate | 10.0% by weight |
| crotamiton | 0.5% by weight |
| acetone | 18.0% by weight |
| ethyl alcohol | 20.0% by weight |
| ethanol | 28.8% by weight |
| ketoprofen | 0.5% by weight |

| Example 70 | liniment |
|---|---|
| 3-l-menthoxypropane-1,2-diol | 2.0% by weight |
| purified water | 10.0% by weight |

The above components were mixed together under agitation, thereby to prepare a liniment comprising ketoprofen.

| Example 71 | liniment |
|---|---|
| polyethyleneglycol 400 | 45.0% by weight |
| 2-hydroxy-4-methoxybenzophenone | 0.5% by weight |
| α-tocopherol | 1.0% by weight |
| isopropylalcohol | 31.5% by weight |
| ethanol | 40.0% by weight |
| ketorolac | 5.0% by weight |
| 3-l-menthoxypropane-1,2-diol | 7.0% by weight |
| purified water | 7.0% by weight |

The above components were mixed together under agitation, thereby to prepare a liniment comprising ketorolac.

| Example 72 | liniment |
|---|---|
| polyethyleneglycol monolaurate | 15.0% by weight |
| 2,2-hydroxy-4-methoxybenzophenone | 0.7% by weight |
| diisopropyl adipate | 4.0% by weight |
| α-tocopherol | 1.0% by weight |
| 8-acetylsucrose denatured alcohol | 49.6% by weight |
| ketorolac | 3.0% by weight |
| 3-l-menthoxypropane-1,2-diol | 5.0% by weight |
| purified water | 21.7% by weight |

The above components were mixed together under agitation, thereby to prepare a liniment comprising ketorolac.

EXAMPLE 73

Aerosol 4.5% by weight of camphor, 4.0% by weight of 3-l-menthoxypropane-1,2-diol, 3.0% by weight of ketoprofen and 1.0% by weight of 2-hydroxy-4-methoxybenzophenone were solubilized in 32.5% by weight of ethanol, incorporated with 26.0% by weight of water, charged into an aerosol container and then incorporated with 4.0% by weight of talc to prepare a pharmaceutical solution, after which a mixed propellant composed of 13.0% by weight of dimethyl ether and 12.0% by weight of liquefied petroleum gas was injected into the container, thereby to obtain an anti-inflammatory and analgetic aerosol. The above weight percentages were respectively based on the whole quantity.

EXAMPLE 74

Aerosol 4.5% by weight of camphor, 0.4% by weight of diphenhydramine, 5.0% by weight of 3-l-menthoxypropane-1,2-diol, 1.0% by weight of ketorolac and 1.0% by weight of α-tocopherol were solubilized in 30.1% by weight of ethanol, incorporated with 24.0% by weight of water to the obtained solution, and then charged into an aerosol container, after which a mixed propellant composed of 25.0% by weight of dimethyl ether and 9.0% by weight of liquefied petroleum gas was injected into the container, thereby to obtain an anti-inflammatory and analgetic aerosol, wherein the ratios were respectively based on the whole quantity.

| Example 75 | creamy-type pack |
|---|---|
| liquid paraffin | 10.0% by weight |
| cetanol | 1.0% by weight |
| sorbitan monostearate | 3.0% by weight |
| POE (20) sorbitan monostearate | 3.0% by weight |
| 1,3-butylene glycol | 5.0% by weight |
| glycerol | 3.0% by weight |
| methyl paraben | 0.2% by weight |
| stearyl glycyrrhetinate | 0.1% by weight |
| 3-l-menthoxypropane-1,2-diol | 1.0% by weight |
| purified water | 73.7% by weight |

The above components were mixed together under agitation, thereby to prepare a cream-type pack.

| Example 76 | clay-type pack |
|---|---|
| kaolin | 20.0% by weight |
| talc | 8.0% by weight |
| glycerol | 3.0% by weight |
| propylene glycol | 3.0% by weight |
| carboxymethyl cellulose | 0.3% by weight |
| POE (20) sorbitan monooleate | 2.0% by weight |
| methyl paraben | 0.1% by weight |
| L-ascorbyl stearate | 0.2% by weight |
| 3-l-menthoxypropane-1,2-diol | 3.0% by weight |
| purified water | 60.4% by weight |

The above components were mixed together under agitation, thereby to prepare a clay-type pack.

| Example 77 | foam-type pack |
|---|---|
| stearic acid | 5.0% by weight |
| behenic acid | 5.0% by weight |
| cetanol | 1.0% by weight |
| squalane | 4.0% by weight |
| glycerol | 15.0% by weight |
| POE (40) monostearate | 1.0% by weight |
| ethyl paraben | 0.1% by weight |
| L-ascorbyl palmitate | 0.05% by weight |
| 3-l-menthoxypropane-1,2-diol | 0.5% by weight |
| purified water | 68.35% by weight |

The above components were mixed together under agitation, thereby to prepare a liquid. Thereafter the liquid was injected with a liquefied petroleum gas into a container to obtain a foam-type pack.

| Example 78 | pressure-sensitive adhesive-type sheet pack |
|---|---|
| gelatin | 8.0% by weight |
| glycerol | 25.0% by weight |
| sorbitol | 7.0% by weight |
| sodium polyacrylate | 2.0% by weight |
| polyvinyl alcohol | 2.0% by weight |
| aluminium hydroxide | 1.0% by weight |
| methyl paraben | 0.05% by weight |
| isopropyl methylphenol | 0.01% by weight |
| 3-l-menthoxypropane-1,2-diol | 0.005% by weight |
| purified water | 54.935% by weight |

The above components were mixed together under agitation, thereby to obtain a paste. The paste was spread on a nonwoven fabric, covered thereon with a release film to obtain a laminate. The laminate was cut into pieces each having a predetermined form to obtain adhesive-type sheet packs.

| Example 78 | impregnation-type sheet pack |
|---|---|
| glycerol | 10.0% by weight |
| 1,3-butylene glycol | 10.0% by weight |
| sodium hyaluroniate | 0.1% by weight |
| methyl paraben | 0.1% by weight |
| glycyrrhizinic acid | 0.01% by weight |
| 3-l-menthoxypropane-1,2-diol | 0.05% by weight |
| purified water | 79.74% by weight |

The above components were mixed together under agitation, thereby to obtain a mixture. The mixture was impregnated into a nonwoven fabric, covered thereon with a release film to obtain a laminate. The laminate was cut into pieces each having a predetermined form to obtain impregnation-type sheet packs.

| Example 80 | peel-off pack |
|---|---|
| polyvinyl alcohol | 20.0% by weight |
| carboxymethyl cellulose | 3.0% by weight |
| titanium oxide | 8.0% by weight |
| 1,3-butylene glycol | 5.0% by weight |
| squalane | 3.0% by weight |
| POE (10) nonylphenyl ether | 0.5% by weight |
| methyl paraben | 0.1% by weight |
| calciferol | 0.01% by weight |
| 3-l-menthoxypropane-1,2-diol | 0.1% by weight |
| purified water | 60.29% by weight |

The above components were mixed together under agitation, thereby to obtain peel-off packs.

COMPARATIVE EXAMPLE 7

Cream-type Pack

The procedure of Example 75 was followed except that the 3-l-menthoxypropane-1,2-diol was not used, thereby to obtain a cream-type pack.

COMPARATIVE EXAMPLE 8

Adhesive-type Sheet Pack

The procedure of Example 78 was followed except that the 3-l-menthoxypropane-1,2-diol was not used, thereby to obtain a adhesive-type sheet pack.

TEST EXAMPLE 1

The plasters of Example 7 and Comparative Examples 4 and 5 were stored at 5° C. for two weeks, while they were observed with the lapse of time to find whether the drug crystallized or not. The results are given in Table 1.

TABLE 1

| Sample | initial | 1 day | 3 days | 7 days | 14 days |
|---|---|---|---|---|---|
| plaster of Ex. 7 | o | o | o | o | o |
| plaster of Comp. | x | x | x | x | x |

TABLE 1-continued

| Sample | initial | 1 day | 3 days | 7 days | 14 days |
|---|---|---|---|---|---|
| Ex. 4 plaster of Comp. Ex. 5 | ○ | x | x | x | x |

○: no crystallization was found
x: crystallization was found

As apparent from the above results, the plaster of Example 7 containing 3-1-menthoxypropane-1,2-diol as the solubilizer contained clonidine in its solubilized state in the base even after the lapse of two weeks, while the plaster of Comparative Example 4 containing no solubilizer and that of Comparative Example 5 containing isopropyl myristate suffered from the crystallization of clonidine in their respective bases. Thus, the above results supported the usefulness of 3-1-menthoxypropane-1,2-diol as the solubilizer for clonidine.

TEST EXAMPLE 2

(Adhesion Test)

The poultices of Examples 1 to 4 and Comparative Examples 1 to 3 were examined for their adhesion and changes thereof time according to the Nichiban Rolling Ball method. This method is such that a ball is so rolled along a poultice sample from a predetermined height at an angle of 30° C. as to draw a sine curve, to measure a distance from a point where the rolling ball reaches the smple to a point where it stops rolling. Accordingly, a shorter distance of roll or a bigger ball means a more excellent adhesion. In this test, a poultice sample having a length of 140 mm was spread with its adhesive side up and a stainless steel ball (20/32 inch, JIS) was rolled along the sample to determine the distance of roll of the ball. The results are given in Table 2.

TABLE 2

| Pressure-sensitive Adhesive tape | Initial adhesion (mm) | After storage for 6 months at 40° C. (mm) |
|---|---|---|
| Ex. 1 | 50 | 48 |
| Ex. 2 | 30 | 33 |
| Ex. 3 | 35 | 38 |
| Ex. 4 | 43 | 41 |
| Comp. Ex. 1 | 98 | 95 |
| Comp. Ex. 2 | 78 | 82 |
| Comp. Ex. 3 | passed through | passed through |

As apparent from the above results, the polutices of Examples 1 to 4 exhibited excellent adhesion and the adhesion did not change even after the lapse of time.

TEST EXAMPLE 3

(Test on Safety for the Skin)

The poultices of Examples 1 to 4 and Comparative Examples 1 to 3 were examined for safety for the skin.

The safety of each poultice for the skin was determined by 25 healthy male and female subjects according to the 48-hour closed patch test. The change in the skin of each subject was determined by observation 1 and 24 hours after the peeling of the patch, and the irritativeness of the poultice was evaluated according to the following criteria. The results are given in Tables 3 and 4.

−: no change in the skin
±: slight rubefaction
+: clear rubefaction
++: heavy contact dermatitis

TABLE 3

| Time which has elapsed after peeling | Judgement Sample | ++ | + | ± | − | Total (subjects) | Rate (%) of positive reaction (±, + and ++) |
|---|---|---|---|---|---|---|---|
| 1 hr | Ex. 1 | 0 | 0 | 0 | 25 | 25 | 0.0 |
| 1 hr | Ex. 2 | 0 | 0 | 1 | 24 | 25 | 4.0 |
| 1 hr | Ex. 3 | 0 | 0 | 0 | 25 | 25 | 0.0 |
| 1 hr | Ex. 4 | 0 | 0 | 0 | 25 | 25 | 0.0 |
| 1 hr | Comp. Ex. 1 | 0 | 0 | 2 | 23 | 25 | 8.0 |
| 1 hr | Comp Ex. 2 | 0 | 0 | 1 | 24 | 25 | 4.0 |
| 1 hr | Comp Ex. 3 | 0 | 0 | 3 | 22 | 25 | 12.0 |

TABLE 4

| Time which has elapsed after peeling | Judgement Sample | ++ | + | ± | − | Total (subjects) | Rate (%) of positive reaction (±, + and ++) |
|---|---|---|---|---|---|---|---|
| 24 hrs | Ex. 1 | 0 | 0 | 0 | 25 | 25 | 0.0 |
| 24 hrs | Ex. 2 | 0 | 0 | 0 | 25 | 25 | 0.0 |
| 24 hrs | Ex. 3 | 0 | 0 | 0 | 25 | 25 | 0.0 |
| 24 hrs | Ex. 4 | 0 | 0 | 0 | 25 | 25 | 0.0 |
| 24 hrs | Comp. Ex. 1 | 0 | 0 | 1 | 24 | 25 | 4.0 |
| 24 hrs | Comp Ex. 2 | 0 | 0 | 0 | 25 | 25 | 0.0 |
| 24 hrs | Comp Ex. 3 | 0 | 0 | 1 | 24 | 25 | 4.0 |

As apparent from the above results, the poultices of Examples 1 to 4 exhibited extremely high safety for the skin.

TEST EXAMPLE 4

(Test on Human Percutaneous Absorption)

The poultices of Example 4 and Comparative Example 2 were each die-cut into samples ($3 \times 3$ cm$^2$). These samples were applied to the upper backs of eight healthy subjects respectively. After 8 hours, the samples were peeled and examined for the amount of ketoprofen remaining in the peeled samples by HPLC (high performance liquid chromatography). The calculation of human absorption rate, the determination of amount of the remaining ketoprofen and HPLC were conducted as follows:

(1) human absorption rate
   =(1—remaining amount/initial content)×100
(2) determination of amount of residue of ketoprofen Each peeled sample was extracted with 70 ml of methanol under reflux and the extract was diluted with methanol to 100 ml. The resulting dilution was used as the sample for HPLC.
(3) Conditions of HPLC
   mobile phase; 0.2% aqueous solution of acetic acid:acetonitrile=55:45
   detection wavelength; 254 nm column; TSK gel ODS-80TM flow rate; 1.0 µl/min.

TABLE 5

| | Human absorption rate (%) |
|---|---|
| Ex. 4 | 12.7 |
| Comp. Ex. 2 | 5.0 |

As shown in Table 5, the poultice of Example 4 containing 3-l-menthoxypropane-1,2-diol as the solubilizer exhibited a higher absorption rate than that of the poultice of Comparative Example 2.

TEST EXAMPLE 5

The plasters of Example 9 and Comparative Example 6 were stored at 5° C., while they were observed with the lapse of time to determine whether crystallization occurred or not. The results are given in Table 6.

TABLE 6

| Sample | initial | 1 day | 3 days | 7 days | 14 days |
|---|---|---|---|---|---|
| Ex. 9 | o | o | o | o | o |
| Comp. Ex. 6 | o | o | x | x | x | o: no crystallization was found
x: crystallization was found

As apparent from the results given in Table 6, the plaster of Example 9 contained diclofenac in a solubilized state in the base even after the lapse of time, though that of Comparative Example 6 containing no solubilizer suffered from the crystallization of diclofenac. Thus, the above results supported the usefulness of 3-l-menthoxypropane-1,2-diol as the solubilizer for diclofenac.

TEST EXAMPLE 6

(Test on Human Pecutaneous Absorption)

The plasters of Example 9 and Comparative Example 6 were each die-cut into samples (3×3 cm²). These samples were applied to the upper backs of six healthy subjects respectively. After 8 hours, the samples were peeled and examined for the residual amount of diclofenac by HPLC. The calculation of human absorption rate, the determination of residual amount of diclofenac and HPLC were conducted as follows:

(1) human absorption rate

=(1—residual amount/initial content)×100

(2) determination of residual amount of diclofenac:

Each peeled sample was subjected to ultrasonic extraction with 30 ml of tetrahydrofuran for 2 hours and the extract was diluted with tetrahydrofuran to 50 ml. The resulting dilution was used as the sample for HPLC.

(3) Conditions of HPLC mobile phase; 0.2% aqueous solution of acetic acid:acetonitrile=1:1 detection wavelength; 275 nm column; TSK gel ODS-80TM flow rate; 1.0 µl/min.

The results are given in FIGURE 1. As apparent from FIGURE 1, the plaster of Example 9 exhibited a significantly enhanced absorption rate as compared with that of Comparative Example 6. In other words, the plaster of Example 9 could contain diclofenac in a solubilized state by virtue of the solubilizability of 3-l-menthoxypropane-1,2-diol thereby to give excellent release of diclofenac.

TEST EXAMPLE 7

The packs of Examples 75 and 78 and Comparative Examples 7 and 8 were stored at 5° C. for two weeks, while they were observed with the lapse of time to determine whether the fat-soluble powder crystallized or not. The results are given in Table 7.

TABLE 7

| | initial | 1 day | 3 days | 7 days | 14 days |
|---|---|---|---|---|---|
| Ex. 75 | o | o | o | o | o |
| Ex. 78 | o | o | o | o | o |
| Comp. Ex. 7 | x | x | x | x | x |
| Comp. Ex. 8 | o | x | x | x | x | o: no crystallization was found
x: crystallization was found

The above results supported the usefulness of 3-l-menthoxypropane-1,2-diol as the solubilizer for a fat-soluble powder.

TEST EXAMPLE 8

The packs of Example 75 and Comparative Example 7 were examined organoleptically by ten female subjects. The results are given in Table 8.

TABLE 8

| | | Ex. 75 | Comp. Ex. 7 |
|---|---|---|---|
| Odor | observed | 0 | 0 |
| | not observed | 10 | 10 |
| Refreshing effect | observed | 10 | 0 |
| | not observed | 0 | 10 |
| Irritation to the skin | observed | 0 | 0 |
| | not observed | 10 | 10 |
| Stickiness | observed | 0 | 1 |
| | not observed | 10 | 9 |
| Roughness | observed | 1 | 8 |
| | not observed | 9 | 2 |

It can be understood from the above results that the pack of Example 75 has refreshing or refrigerant effect and is freed from the crystallization of a fat-soluble powder thereby to be excellent in feelings in use.

Industrial Applicability

According to the present invention, 3-l-menthoxypropane-1,2-diol which has been used as a refrigerant is used as a solubilizer for a pharmaceutically effective ingredient and this compound exhibits high solubilizability for a pharmaceutically effective ingredient and is excellent in safety, stability and compatibility. Accordingly, a percutaneously absorbable preparation (which is one of external preparations) containing said compound is improved in the release of a pharmaceutically effective ingredient from the base and the pecutaneous absorption of the effective agent. Further, such a preparation causes little side effects such as contact dermatitis even when applied repeatedly and is not irritant to the skin thereby to be extremely safe. Furthermore, the preparation is odorless and can impart comfortable refreshing refrigeration to the skin.

Accordingly, the external preparation of the present invention is suited for percutaneously absorbable preparations and packs, thus having high industrial applicability.

What is claimed is:

1. A percutaneously absorbable preparation which comprises, by weight, 0.001 to 20% of 3-1-menthoxypropane-1,2-diol as a solubilizer for a drug and 0.001 to 20% of said drug, the balance being other ingredients as adjuvants for said preparation.

2. The preparation according to claim 1 wherein the content of 3-1-menthoxypropane-1,2-diol is 0.1 to 20% by weight.

3. The preparation according to claim 1 which is in a form selected from the group consisting of a poultice, a plaster, an ointment, a gel, a cream, a gel cream, a lotion, a reservoir patch, a liniment and an aerosol.

4. The preparation according to claim 3 which is a poultice wherein said balance comprises a water-soluble polymer, a polyhydric alcohol and water.

5. The preparation according to claim 3 which is a plaster wherein said balance comprises a) a member selected from the group consisting of a rosin ester, a styrene-isoprene-styrene block copolymer and an acrylic adhesive and (b) a softening agent, in the amount of 150–350 parts by weight per 100 parts of said styrene-isoprene-styrene block copolymer, the amounts by weight of said drug, said rosin ester and said 3-1-menthoxy-propane-1,2-diol being 1:(2 to 25):1 to (10).

6. The preparation according to claim 3 which is an ointment wherein said balance comprises a higher fatty acid or an ester thereof, a wax, a surfactant a vaseline, and liquid paraffin.

7. The preparation according to claim 3 which is a gel, wherein said balance comprises a lower alcohol, water, a gelling agent and a neutralizing agent.

8. The preparation according to claim 3 which is a cream wherein said balance comprises a higher fatty acid ester, water, a hydrocarbon which is a vaseline, or liquid paraffin and an emulsifying agent.

9. The preparation according to claim 3 which is a gel cream wherein said balance comprises a higher fatty acid ester, a lower alcohol, water, liquid paraffin, an emulsifying agent, a neutralizing agent and a gelling agent.

10. The preparation according to claim 3 which is a lotion wherein said balance comprises a lower alcohol, water and a glycol.

11. The preparation according to claim 3 which is a reservoir patch which comprises (1) a backing layer; 2) a drug reservoir layer; 3) a drug releasing layer; 4) a pressure-sensitive adhesive layer, said drug-reservoir layer 2) has said 3-1-menthoxy propane-1,2-diol and a base, said base comprises (a) a mixture comprising a glycol, a lower alcohol, water and a water-soluble polymer; (b) a mixture comprising an aliphatic monohydric alcohol or a polyhydric alcohol or both a monohydric alcohol and a polyhydric alcohol or (c) a mixture comprising paraffin and a silicon compound.

12. The preparation according to claim 3 which is a liniment wherein said balance comprises an alcohol, water and a fatty acid ester.

13. The preparation according to claim 3 which is an aerosol wherein said balance comprises a lower alcohol, water, dimethyl ether or liquefied petroleum gas or both dimethyl ether and liquefied petroleum gas.

14. The preparation as set forth in claim 4 which comprises, by weight, 0.1 to 20% of said solubilizer, 0.5 to 10% of said drug, 1–30% of a water-soluble polymer, 10 to 90% of a polyhydric alcohol and 10 to 90% of water.

15. The plaster according to claim 5 which comprises, by weight, 0.5 to 10% of 3-1-menthoxypropane-1,2-diol, 0.5 to 10% of said drug, 5 to 70% of said rosin ester, 5 to 40% of said styrene-isoprene-styrene block copolymer and 10–75% of said softening agent.

16. The ointment according to claim 6 which comprises, by weight, 0.5–10% of 3-1-menthoxypropane 1,2-diol, 0.5–10% of said drug, 5–15% of said higher fatty acid or the ester thereof, 4–10% of said wax, 1 to 10% of said surfactant and 50–90% of said hydrophilic vaseline.

17. The ointment according to claim 16 wherein said higher fatty acid is myristic acid and the ester of said higher fatty acid is glycerol monostearate, isopropyl myristate or diethyl sebacate, said wax is selected from the group consisting of spermaceti and beef tallow, and said hydrocarbon is hydrophilic vaseline.

18. The gel according to claim 7 which comprises, by weight, 0.5 to 10% of 3-1-menthoxypropane-1,2-diol, 0.5 to 10% of the drug, 0.5 to 5% of said gelling agent, at the most 60% of the lower alcohol, at the most 40% of the glycol, 0.2 to 2.5% of the neutralizing agent and at the most 55% of water.

19. The gel according to claim 18 wherein said gelling agent is a carboxyvinyl polymer, said lower alcohol is ethanol, and said neutralizing agent is triethanolamine or diisopropanolamine.

20. The gel cream according to claim 9 which comprises, by weight, 0.5 to 10% of 3-1-menthoxypropane-1,2-diol, 0.5 to 10% of said drug, at most 25% of the higher fatty acid ester, at most 40% of the lower alcohol, at most 5% of said emulsifying agent, 0.5 to 5% of said gelling agent, the balance being purified water.

21. The gel-like cream according to claim 20 wherein said higher fatty acid ester is isopropyl myristate, isopropyl palmitate or polyethylene glycol monostearate, said lower alcohol is ethanol, said gelling agent is a carboxyvinyl polymer, and said neutralizing agent is triethanolamine or diisopropanolamine.

22. The lotion according to claim 10 wherein said lower alcohol is ethanol and said glycol is propylene glycol.

23. The liniment according to claim 12 which comprises, by weight, 0.5 to 10% of said 3-1-menthoxypropane-1,2-diol, 0.5 to 10% of said drug, 10 to 70% of said alcohol, at most 55% of water and at most 60% of said fatty acid ester.

24. The liniment according to claim 23 wherein said alcohol is ethanol, isopropanol, or propylene glycol, said fatty acid ester is a member selected from the group consisting of polyethylene glycol laurate, 3-acetylated sucrose denatured alcohol and diisopropyl adipate.

25. The preparation according to claim 1 wherein the drug is a member selected from the group consisting of a steroidal anti-inflammatory agent, a nonsteroidal anti-inflammatory agent, an antiallergic agent, an antihistaminic agent, a central nervous system stimulant, a hormone, an antihypertensive agent, a cardiotonic agent, an antiarrhythmic agent, a coronary vasodilator, a local anesthetic, an analgesic agent, a skeletal muscle relaxant, an antifungal agent, an antineoplastic agent, an antidysuric agent, an antiepileptic agent, an antiparkinson agent, a smoking-prohibition assistant agent, a vitamin, and prostaglandin.

26. The preparation according to claim 1 wherein the drug is a fat soluble powder in the amount of 0.001–20%, the preparation is a pack and comprises, by weight, 0.001 to 5% of 3-1-menthoxy-propane-1,2-diol as a solubilizer and said fat soluble powder is a member selected from the group consisting of glycyrrhetinic acid, stearyl glycyrrhetinate, glycyrrhizinic acid, L-ascorbyl stearate, L-ascorbyl palmitate, calciferol, cholecalciferol, pionin and isopropylmethylphenyl the balance being other ingredients as adjuvants for the preparation.

27. The preparation according to claim 26, wherein said balance comprises glycerol, liquid paraffin, methyl paraben and purified water.

* * * * *